United States Patent [19]

Rusch et al.

[11] Patent Number: 4,818,763

[45] Date of Patent: Apr. 4, 1989

[54] BIOLOGICALLY ACTIVE SUBSTANCE WITH HORMONAL PROPERTIES, PRODUCTION PROCESS THEREOF AND UTILIZATION OF HISTONES FOR MEDICAL PURPOSES

[75] Inventors: Volker Rusch, Schwalbenweg 6, 6348 Herborn; Robert Reichhart, Homburg/Saale; Michael Zeppezauer, Saarbrücken-Scheidt, all of Fed. Rep. of Germany; Hans Jörnvall, Sundbyberg, Sweden

[73] Assignee: Volker Rusch, Herborn, Fed. Rep. of Germany

[21] Appl. No.: 777,783

[22] PCT Filed: Jan. 10, 1985

[86] PCT No.: PCT/DE85/00004

§ 371 Date: Sep. 12, 1985

§ 102(e) Date: Sep. 12, 1985

[87] PCT Pub. No.: WO85/03003

PCT Pub. Date: Jul. 18, 1985

[30] Foreign Application Priority Data

Jan. 12, 1984 [DE] Fed. Rep. of Germany ....... 3400928
Feb. 16, 1984 [DE] Fed. Rep. of Germany ....... 3405620

[51] Int. Cl.$^4$ ..................... A61K 37/00; A61K 37/48
[52] U.S. Cl. .................................... 514/2; 424/94.1; 530/358; 514/885
[58] Field of Search .................. 514/2, 885; 424/94.1; 530/358

[56] References Cited

U.S. PATENT DOCUMENTS 4,415,553 11/1983 Zhabilov et al. .................... 424/95

FOREIGN PATENT DOCUMENTS

| 0101063 | 2/1984 | European Pat. Off. | |
|---|---|---|---|
| 2732587 | 3/1978 | Fed. Rep. of Germany | 514/2 |
| 2265404 | 10/1975 | France | 514/2 |
| 2305191 | 10/1976 | France | 514/2 |
| 2315943 | 1/1977 | France | 514/2 |

OTHER PUBLICATIONS

Biol. Abst. 73:80609, 1973.
Bezssonoff, N. A. & Comsa, J. (1958) Ann. Endocr. 19, 222-227, in English in Acta Endocrinologica 29, 257-266, 1958.
Bernardi, G. & Comsa, J. (1965) Experientia 21, 416-417.
Comsa, J. (1965) Am. J. Med. Sci. 250, 79-85.
Comsa, J. & Filipp. G. (1966) Ann. Instit. Pasteur 110, 365-372.
Comsa, J. (1973) in Thymic Hormones, ed. Luckey, T. D., University Press, Baltimore, pp. 39-58, 59-96.
Comsa, J., Leonhardt, H. & Wekerle, H. (1982) Rev. Physiol. Biochem. Pharmacol. 92, pp. 1, 166-168, 191.
Comsa, J., Baumann, B., Zeppezauer, M., Leonhardt, H. & Weber, N. (1979) C. R. Acad. Sc. Paris 288, 185-187.
Low, T. L. K. & Goldstein, A. L. (1979) J. Biol. Chem. 254, 987-995.

(List continued on next page.)

Primary Examiner—John W. Rollins
Attorney, Agent, or Firm—Weiser & Stapler

[57] ABSTRACT

Biologically active substance with standardizable hormonal activity, containing in a physiological medium at least one histone, particularly at least one histone H2 or an active area of said histone with immune system immunostimulating and/or endocrinological properties. Utilization of histones and/or segments of histones for producing such a preparation for medical purposes. Said histones may be extracted from biological starting materials, for example calf thymus. Since H2A and H2B histones of oxen and humans are identical, ox histones may also be used for such a preparation for human medical purposes. The preparation according to the present invention may also contain only the variable evolution segments or part of at least one H2 histone. The invention is based on the fact that the biologically active area of an immunostimulating or endocrinologically active histone is located in the variable evolution histone segment. The preparation according to the present invention may be used in immunotherapy.

23 Claims, 4 Drawing Sheets

OTHER PUBLICATIONS

Reichhart, R., Jornvall, H. & Zeppezauer, M. (1984) FEBS Lett., FEBS Letters, 188, 63–67, 1985.
DeLange, R. J., Hooper, J. A. & Smith, E. L. (1972) Proc. Natl. Acad. Sci. USA 69, 882–884.
Olson, M. O. J., Jordan, J. & Busch, H. (1972) Biochem. Biophys. Res. Commun. 46, 50–55.
Kanda, Y., Goodmann, D. S., Canfield, R. E. & Morgan, F. J. (1974) J. Biol. Chem. 249, 6796–6805.
Jornvall, H., Mutt, V. & Persson, M. (1982) Hoppe-Seyler's Z. Physiol, Chem. 363, 475–483.
Ball, D. J., Slaughter, C. A., Hensley, P. & Garrard, W. T. (1983) FEBS Lett. 154, 166–170.
Hahn, G. S. & Hamburger, R. N. (1981) J. Immunol. 126, 459–462.
Moss, T., Cary, D. P., Abercrombie, B. D., Crane-Robinson, C. & Bradbury, E. M. (1976) Eur. J. Biochem. 71, 337–350.
Jornvall, H., Ekman, R., Carlquist, M. & Persson, B. (1984) in Biogenetics of Neurohormonal Peptides (Eds.: Hakanson, R. & Thorell, J.) Academic Press, London, in press (1984).
Bohm, L., Briand, G., Sautiere, P. & Crane-Robinson, C. (1982) Eur. J. Biochem. 123, 299–303.
Bohm, L., Crane-Robinson, C. & Sautiere, P. (1980) Eur. J. Biochem. 106, 525–530.
Rill, R. L. & Ooosterhof, D. K. (1982) J. Biol. Chem. 257, 14875–14880.
Eickbush, T. H., Watson, D. K. & Moudrianakis, E. N. (1976) Cell 9, 785–792.
Isenberg, I. (1979) Ann. Rev. Biochem. 48, 159–191.
Yeaman, S. J., Cohen, P., Watson, D. C. & Dixon, G. H. (1977) Biochem. J. 162, 411–421.
West, M. H. P. & Bonner, W. M. (1980) Nucl. Acids Res. 8, 4671–4680.
Caldarella, J., Goodall, G. J., Felix, A. M., Heimer, E. P., Salvin, S. B. & Horecker, B. L. (1983) Proc. Natl. Acad. Sci. USA 80 7424–7427.
Low, T. L. K., Hu, S. K. & Goldstein, A. L. (1981) Proc. Natl. Acad. Sci. USA 78, 1162–1166.
Hannappel, E., Davoust, S. & Horecker, B. L. (1982) Proc. Natl. Acad. Sci. USA 79, 1708–1711.
Audhya, T., Schlesinger, D. H. & Goldstein, G. (1981) Biochemistry 20, 6195–6200.
Pleau, J. M., Dardenne, M., Blouquit, & Bach. J. F. (1977) J. Biol. Chem. 252, 8045–8047.
Hershko, A. (1983) Cell 34, 11–12.
Schlesinger, D. H., Goldstein, G. & Niall, H. D. (1975) Biochemistry 14, 2214–2218.
Burton, P., Iden. S., Mitchell, K. & White, A. (1978) Proc. Natl. Acad. Sci. USA 75, 823–827.
Jornvall, H., Carlstrom, A., Pettersson, T., Jacobsson, B. Persson, M. & Mutt, V. (1981) Nature 291, 261–263.
Robey, G., Campbell, B. J. & Luckey, T. D. (1972) Infection a. Immunity 6, 682–688.
Haritos, A. A., Goodall, G. J. & Horecker, B. L. (1984) Proc. Natl. Acad. Sci. USA 81; 1008–1011.
Pradayrol, L., Jornvall, H., Mutt, V. & Ribet, A. (1980) FEBS Lett. 109, 55–58.
Jornvall, H. & Persson, B. (1983) Biosci. Rep. 3, 225–232.
Grove, G. W. & Zweidler, A., (1984) Biochemistry 23, 4436–4443.
Jordano, J., Montero, F. & Palacian, E. (1984) Biochemistry 23, 4380.
Hannestad, K. & Stollar, B. D. (1978) Nature 275, 671–673.
Rekvig, O. P. & Hannestad, K. (1980) J. Exp. Med. 152, 1720–1733.
Williams, A. F. (1984) Nature 308, 12–13.

H2A: I E L A G N A R D N K K T R I I P R H L Q L A I R N D E E L N
     (positions 70, 80, 90)

H2B: I A G E A S R L A H Y N K R S T I T S R E I Q T A V R L L L P G E
     (positions 80, 90, 100)

H3:  L F E D T N L C A I H A K R V T I M P K D I E L A R R I R G E R A
     (positions 110, 120, 130)

FIG. 3A

| PROTEIN | SEGMENT | AMINO ACID SEQUENCE |
|---|---|---|
| H3 | 17-29 | R K Q L A T K A - - - A R K S A |
| H2B | 14-26 | S K K A V T K A - - - Q K K D G |
| H2A | 11-23 | R A K A K T R S - - - S R A G L |
| H2A.Z. | 9-25 | S G K A K T K A V S X Q R A G L |
| THYMOPOIETIN | 21-35 | - A N N V T L P A G E Q R K D V |
| THYMOSIN $\alpha_{11}$ | 19-33 | K K E V V E E A - E N G R E A P |
| THYMOSIN $\beta_9$ | 23-37 | Q E K N - T L P T K E T I E Q E |
| UBIQUITIN | 10-22 | - G K T I T L - E V E - P S D T |
| | | |
| THY-1 | 66-80 | F I K V L T L A - N F T T K D E |
| IgE | 497-111 | S R L E V T R A - E W Q E K D E |
| IgG | 408-222 | S K L S V P T S - E W Q R G D V |
| HLA | 245-259 | A A V V V P S G - E E Q R Y T C |
| B$_2$-m | 64-78 | L L Y S Y T E F - T P T E K D E |

FIG. 3B

BIOLOGICALLY ACTIVE SUBSTANCE WITH HORMONAL PROPERTIES, PRODUCTION PROCESS THEREOF AND UTILIZATION OF HISTONES FOR MEDICAL PURPOSES

Numerous and various thymus preparations are known. They also include the thymus preparation (HTH) according to Comsa & Bernardi ("Extraction, Fractionation and Testing of a Homogeneous Thymic Hormone Preparation", published in *Annals of the New York Academy of Sciences*, Vol. 240, Feb. 28, 1975, pp. 402–403).

Cosma was able to show, among other things, that HTH possesses immune system-immunostimulating and endocrinologically active properties. He suspected that this effect can be attributed to a special thymic hormone ("Hormonal Coordination of the Immune Response", Vol. 92, Springer-Verlag, 1982). Comsa also demonstrated that thymus preparations can be therapeutically ineffective or detrimental due to unclarified side effects of substances that are yet to be identified. Consequently, thymic preparations may contain substances which conceal or inhibit or interfere with the effective properties of the presumed thymic hormone within the thymic preparation and which can represent a considerable risk for the patient.

An objective of the present invention is to propose a biologically active substance of the above-described type which shows a clear relationship to the desired thymic hormone-like effect, i.e., is essentially free from foreign substances which can adversely affect this effect. The purpose primarily pursued herewith is mainly to create the possibility to standardize the effect of such a preparation and thus to open up ways for processes for the production of the active substance from bilogical starting materials, which practically yield pure preparations with hormone-like effects, which are free from foreign substances.

The task is accomplished by the invention characterized in the claims.

Figure 3A:
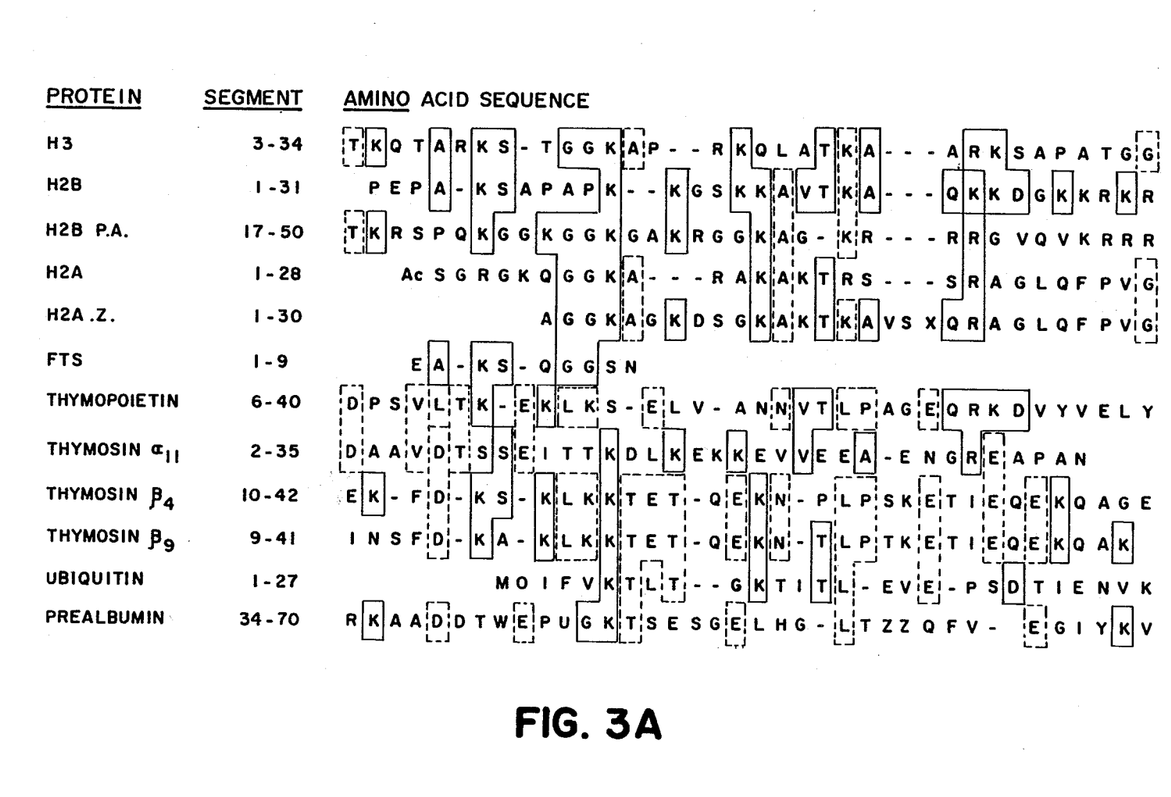
Figure 3B:
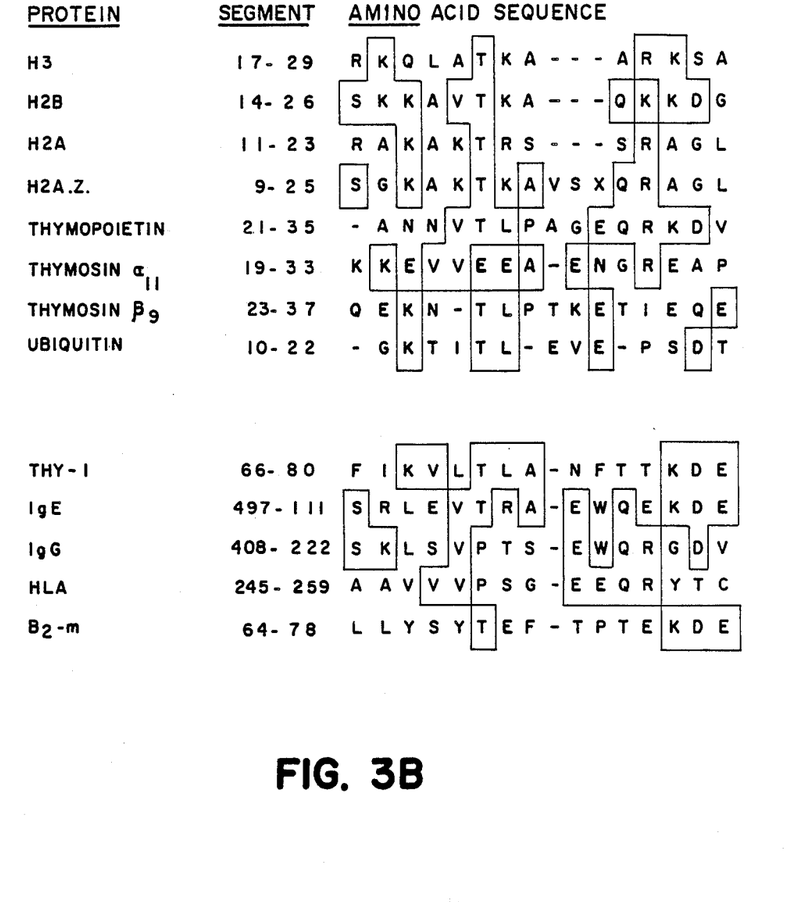

It was surprising for the inventors that they were unable to localize any specific thymic hormone possessing clearly immunological and endocrinological properties in the Comsa-Bernardi HTH thymus fraction. On investigations of HTH, it was possible to prepare two reproducibly detectable polypeptide chains, $HTH_a$ and $HTH_B$ as the hormonal active substances, whose aminoacid sequences surprisingly proved to be identical with the sequences of the H2A and H2B histones. The inventors were thus able to show for the first time ever that histones which had previously been known only as cell-nucleus proteins must possess hromone-like properties with extracellular and endocrine activities. Histone/thymic hormone structural comparisons showed that the hormone-like, especially thymic hormone-like properties of the histones are determined, at least essentially to a major extent, by the variable evolution parts of the histones (following description and FIG. 3 (A)) and that they cannot be found in the invariable evolution (constant) portions of the histone. The inventors were able to localize component sequences with hormonal effect (active histone sequences) by the structural comparisons in the variable evolution-histone segments of the H2 histones (following description and FIG. 3 (B)), which show similarities with thymic hormones. It was also possible to show that similarities especially exist with the N-terminal histone areas and interchangeable relationship which exist between histones and proteins of the immune system, especially ubiquitin.

Thus, it is disclosed in the present invention that histones, especially H2A and H2B histones and certain segments thereof possess hormone-like, especially thymic hormone-like properties and are not only constituents of the cell nucleus. It was also found that the immune system-immunostimulating and/or endocrinologically active substances, which are contained in the great variety of known thymus preparations, show similarities with the variable evolution segments of the histones and can therefore probably be included in a histone family which may have to be redefined concerning its newly discovered hormonal properties.

Thus, the present invention discloses relatively simple ways for the specific production of immune system-immunostimulating and/or endocrinologically active preparations with a preparation whose effect that has now become standardizable for the first time ever. Thus, it is no longer necessary to isolate specific peptides possessing the desired effect from thymus preparations alone, because it is also possible to prepare preparations from other biological starting materials which are particularly rich in isolatable histones, especially H2A and H2B histones.

Since it has become known meanwhile that H2A and H2B calf histones are identical with human H2A and H2B histones, it is fully unobjectionable to prepare preparations according to the present invention for human medicine, e.g., from calf thymus or from another suitable endocrine organ of the calf or ox which is rich in H2A and H2B histones in association with a physiological medium.

The discovery that the immune system-immunostimulating and/or endocrinologically active properties of the histones is important for the commercial preparation of the preparations according to the present invention by synthesis. It is therefore sufficient to only synthesize the variable evolution segments of the histones in question or of parts thereof, which contain the active sequence. This also applies to the preparation or combination of these production processes according to genetic engineering methods.

Therefore, the present invention is not restricted to the use of histones, especially H2A and H2B histones as immunostimulating and endocrinologically active preparations. It is also possible to use the variable evolution segments or the active areas of these variable evolution segments or a combination of one or more of such segments with one or more histones.

Finally, the present invention is not restricted to the use of histones or histone segments possessing hormone-like properties. Thus, the application of such histones or histone segments with at least one protein of the immune system, such as ubiquitin, can be especially advantageous according to the present invention.

According to the present invention, "histones" are more broadly defined in view of their recently discovered hormonal properties than in the conventional sense of the word according to which histones were considered to be only constituents of the cell nuclei.

The effect of histone as an immunostimulating substance and synergist and/or antagonist of endocrine glands (endocrinological activity), which was recognized by the inventors, presupposes that the histones are fully or at least partly in the form of component sequences which are responsible for the newly discovered effect and circulate in the bloodstream and/or lymphatic system in order to be able to exert their hormonal effects. No such effect was to be expected according to the previous definition of the histones.

The underlying discoveries of the present invention concerning the properties of the histones and the related studies on the homeostatic thymic hormone (HTH) will be described below in more detail. The figures in parentheses refer to the list of references at the end of the description which also contains figures illustrating the results of the investigations. In the Figures:

FIG. 1 (A) shows the purification of the HTH preparation according to Bernardi and Comsa [2] by HPLC on a $\mu$ Bondapak-C18 column in 0.1% trifluoroacetic acid using isopropanol gradient (% B). Within FIG. 1 (A) is shown an SDS polyacrylamide gel electrophoresis of (a) HTH starting material and (b) the HTH$_\alpha$ and HTH$_\beta$ components of the HTH fraction C;

FIG. 1 (B) shows the fractionation of the HTH fraction C (FIG. 1 (A)) into the two components HTH$_\alpha$ and HTH$_\beta$ by HPLC on a $\mu$ Bondapak-C18 column in 0.1% trifluoroacetic acid using acetonitrile gradient (% B);

FIG. 3 (A) shows comparisons of the amino-acid sequences of a first group of histones with a second group of thymic hormones: the histones H3 (from calves [37]), H2B (from calves and humans [37], H2B P.A. (sperm of the sea-urchin *Parechinus angulosus* [37]), H2A (from calves and humans [37]) and H2A.Z (variant of calf [28]). FTS is a thymic serum (from pigs [14]). Thrombopoietin (from oxen [13]), thymosin $\alpha_{11}$, $\beta_4$ and $\beta_9$ (from calves [10–12]), ubiquitin (from oxen [16]) and prealbumin (from humans [17]). Identical amino acids between the two groups are enclosed between solid lines. Amino acids which are identical only within one of the two groups are enclosed between broken lines. Sequence interruptions (gaps) were made in order to illustrate the maximum structural agreements.

FIG. 3 (A) basically shows the variable evolution-histone segments of the H2A and H2B histone segments (H2A basically includes the amino acids 1 through 36, and H2B approximately includes the amino acids 1 through 31). The active sequences which are especially essential for the present invention are located within these segments.

FIG. 3 (B): further comparisons of amino-acid sequences of the two protein groups in FIG. 3 (A) with cell-surface antigen (from rats (Thy-1)), immunoglobulin (from humans and rabbits (IgE and IgG)), histocompatibility antigen (from humans (HLA-B7)) and $\beta_2$-microglobulin (from humans $\beta_2$-m)). Identical amino acids are located between solid lines.

FIG. 3 (B) shows, among other things H2A and H2B segments within the variable evolution-histone segments (H2A amino acids 11 through 23, H2B amino acids 14 through 26), which can be important for the further identification of the active sequences according to the present invention.

Various functions of the thymus have been clearly demonstrated: they include the proliferation and differentiation of the lymphoid precursor cells as well as the production and secretion of various thymic hormones. One of these hormones, the homeostatic thymic hormone (HTH), was discovered, as was mentioned in the introduction, at an early date by Comsa et al. [1, 2]. HTH was reported to completely suppress the consequences of thymectomy [3], to restore antibody production in thymectomized animals [4] and to exert a chemotactic effect on lymphocytes [5]. It was also possible to show the regulatory effect of HTH on other endocrine glands [6, 7]. Thus, HTH is an antagonist of thyroxine [6], the adrenocorticotropic hormone (ACTH), deoxycorticosterone, thyrotropin (TSH) and of the gonadotropins. HTH is a synergist of the growth hormone [6, 7]. Radioprotective effect of HTH was also additionally proposed [8].

HTH was found in the thymus, the lymph nodes and in the spleen of normal rats prior to puberty. It was reported that it completely disappears from the lymph nodes and the spleen three days after thymectomy [5, 6]. It was possible to isolate a fraction similar to HTH from human urine, which prevented the consequences of thymectomy in guinea pigs. This thymus-substituting fraction was absent in the urine of a girl who had previously been subjected to complete thymectomy [5]. Thus, various facts prove that HTH is secreted, distributed in the body and excreted.

It has not yet been possible to clarify the structure of HTH. However, some other polypeptides of the thymus were also characterized; they include several thymosins [9–12], thymopoietins [13] and the small nonapeptide "serum thymic factor" (FTS) [14]. After isolation from the thymus, the structure of the protein ubiquitin was also determined, the probable influence of this protein on the regulation of the protein catabolism is now known [15]. The identity of the "serum thymic hormone" with serum prealbumin, which shows a possible relationship with the gastrointestinal hormone [18], was also established [17].

When the differences in the sizes of the thymic hormones are taken into account, which range from the small polypeptides to the lymphocyte-stimulating hormone (LSH$_r$, M$_r$ 80,000) [19] and other large proteins, it seems to be possible that some chains are fragments of larger proteins. This assumption was corroborated by the recently discovered thymosin $\alpha_{11}$ which contains seven amino acids in addition to those of the thymosin $\alpha_1$, and by prothymosin which contains ca. 112 amino acids, which contains the thymosin $\alpha_1$ sequence in its amino terminal group [20]. Furthermore, a Lys-Arg structure, which is a typical signal for the prohormone cleavage [21, 22], is also present at the C-terminal ends of all thymopoietins [13]. It can be stated in summary that several thymic hormones have been characterized in addition to HTH. Cleavages of the pro forms seem to be important, but only a few reactions and no structural relationships have been demonstrated so far.

The practically complete purification and yield of two components, HTH$_\alpha$ and HTH$_\beta$, which were the only reproducibly detectable polypeptide chains of the HTH preparations according to the inventors, will be described below. The amino acid sequences of HTH$_\alpha$ and HTH$_\beta$, whose determinations are separately described by the inventors [23], were found by the inventors to be identical with the sequence of the histones H2A and H2B. Since no extracellular or endocrine activites of histones have become known so far, the inventors investigated the possibility that H2A and H2B are mere impurities in the HTH preparations. However, it was found that HTH$_\alpha$ and HTH$_\beta$ are the only components which were able to be enriched in HTH preparations. If the two components had not constituted the HTH themselves, the HTH activity would have had to be due to a component which should only be present in very slight quantities and which should have been able to be purified together with the histones. In view of this possibility, the inventors thoroughly investigated the HTH$_\alpha$/H2A and HTH$_\beta$/H2B structures, doing so primarily in relation to possible cleavage signals and similarities with other thymic hormones. Based on these relationships, new and surprising histone functions were discovered which also explain how HTH and also perhaps other thymic hormones cooperate with histones and ubiquitin in a regulatory system. The application of histones according to the present invention in drugs was actually opened up by these functions.

Figure 1A:
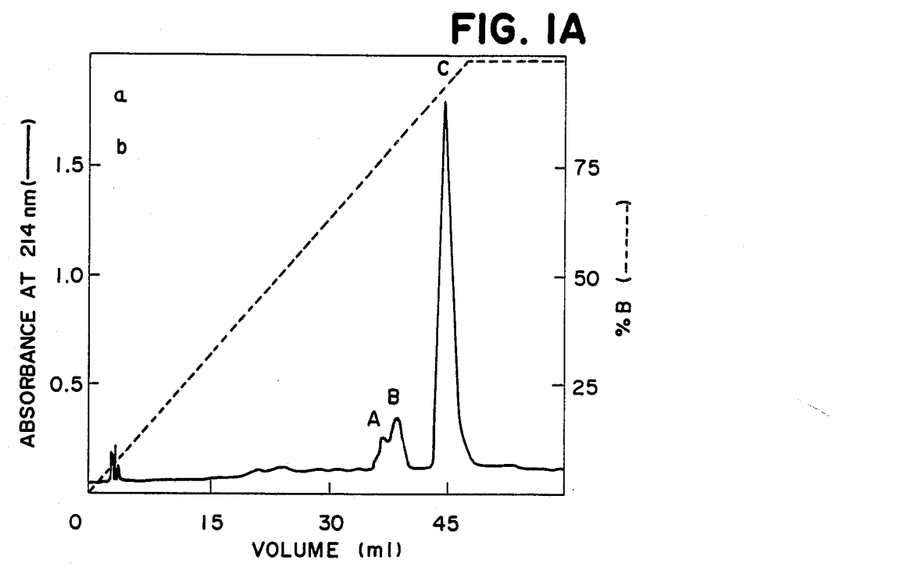
Figure 1B:
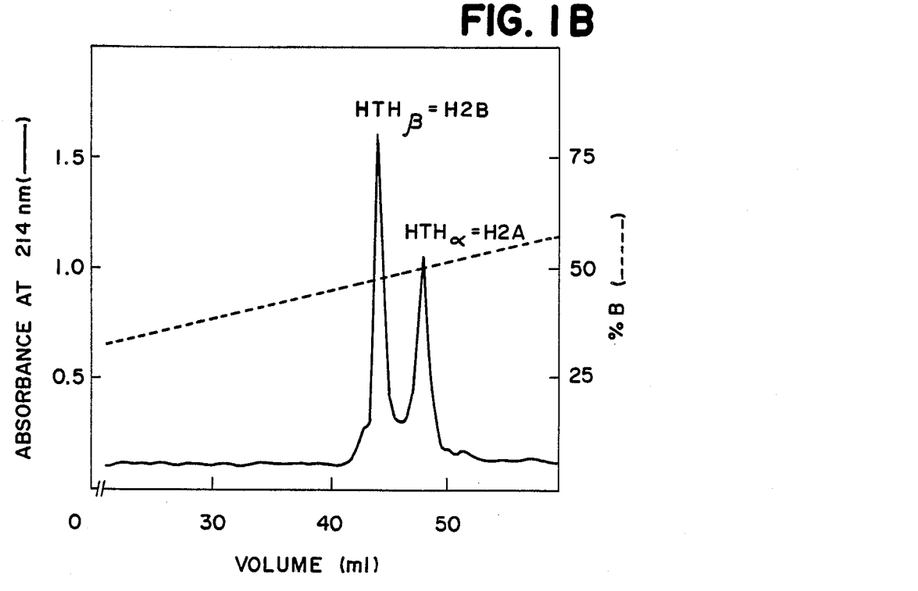

Purification of HTH (FIGS. 1 (A) and 1 (B))

The homeostatic thymic hormone HTH was isolated from calf thymus using a five-step purification method which consists, as was described in [1], of precipitations of an acidic extract (1M H$_2$SO$_4$) with ammonium sulfate and ethanol and subsequently chromatographic separations on Sephadex G-100, hydroxyapatite and Sephadex G-25 [2]. The purification was hindered by proteolytic effects until an enzyme inhibitor was added. These fractions were active in the biological tests described in the introduction above. The final purification of two components with the respective $M_r$ of 15,000 and 16,500 was carried out by HPLC on a Waters instrument with a Bondapak-C18 column using isopropanol or acetonitrile gradients in 0.1% trifluoroacetic acid.

Amino-acid-sequence analysis

HTH was split with CNBr and with proteolytic enzymes [23]. The peptide mixtures were subjected to preliminary fractionation over Sephadex G-50 fine in 30% acetic acid and were subjected to further purification as described above to obtain the intact HTH components.

The dimethylaminoazobenzene method was used for the manual sequence analysis. The liquid-phase sequence decomposition was carried out with a Beckman 890D model instrument using a 0.1M quadrol-peptide program in the presence of glycine-pretreated Polybrene. The phenylthiohydantoins were identified by HPLC [23].

Sequence comparisons

The amino-acid sequences determined for HTH$_\alpha$/Ha2 and HTH$_\beta$/H2B were compared with those of the histone H3 [24, 25], the thymosins [9–12], the thymopoietins [13], FTS [14], ubiquitin [16] and prealbumin [26]. Using different segment sizes, a computer program was used to detect similarities regardless of the sequence gaps and using random structures of the same composition in order to estimate the degree of accidentally similar structures.

Results of the purification of HTH

In the case of isolation without proteolysis, the biologically active HTH preparation of Bernardi and Comsa [2] contained no small peptides. On SDS polyacrylamide gel electrophoresis in a 7.5% gel under reducing and nonreducing conditions, this preparation always had two constantly present peptide bands corresponding to $M_r$ 15,000 and $M_r$ 16,500 [FIG. 1 (A)]. The determination of the molecular weight of the native HTH by exclusion chromatography on Sephadex indicated a value of ca. 30,000, which suggests that the native HTH is dimeric. Contrary to reports according to which HTH could be a glycoprotein [5] and cannot be precipitated with trifluoroacetic acid [1], the inventors found partly carbohydrates and partly a protein which can be precipitated with trifluoroacetic acid.

In order to separate the two principal polypeptide chains from minor and varying impurities, the HTH preparations were separated by HPLC using isopropanol gradient. The two components were eluted in a main peak which is designated by C in FIG. 1 (A). This peak is preceded by two smaller peaks (A and B). These smaller peaks correspond to variable quantities of several components with electrophoretic positions (FIG. 1 (A)) which are identical with the inactive components from the preceding purification steps. The SDS polyacrylamide gel electrophoresis of the samples from fraction C under reducing and nonreducing conditions confirmed the existence of two main peptide components (FIG. 1 (A)). However, the determination of the terminal groups according to the Dansyl method only showed proline as the N-terminal amino acid (the second polypeptide chain has a blocked N terminal). HPLC using a soft acetonitrile gradient permitted the separation of the fraction C into two components, HTH$_\alpha$ and HTH$_\beta$, in pure form (FIG. 1 (B)), which was confirmed by SDS polyacrylamide gel electrophoresis. The amino-acid sequences of the two proteins were determined by sequence decomposition in connection with fragmentation by CNBr and proteolytic enzymes as was described in [23]. They showed that HTH$_\alpha$ is identical with the histone H2A and HTH$_\beta$ is identical with the histone H2B. The inventors did not observe any sign of modification of the amino acids in the HTH [23].

Comparison with other sequences (FIGS. 3 (A) and 3 (B))

The structures of HTH$_\alpha$/H2A and HTH$_\beta$/H2B were investigated with respect to similarities with the thymosins $\alpha_1$, $\alpha_{11}$, $\beta_4$, $\beta_9$ [9–12], the thymopoietins [13], the histones H2A, H2B, H3 and the subtype H2A.Z [28], ubiquitin [16] and prealbumin [26] in order to identify proteins which are functionally related either with the thymic hormones or the histones. Using variable fragment sizes [27], a computer program showed that no remarkable similarities exist, and that none of the pairs compared shows any significant similarities with each other in itself. Seven of the 15 best fits (those with 6 and 7 identical amino acids per 15 amino acids) between H2A-H2B, H2A-H3 and H2B-H3 do orient, however, independent of each other, the C-terminal regions of these histones in such a way relative to each other (FIG. 2) that the best possible agreement is obtained.

Figure 2:
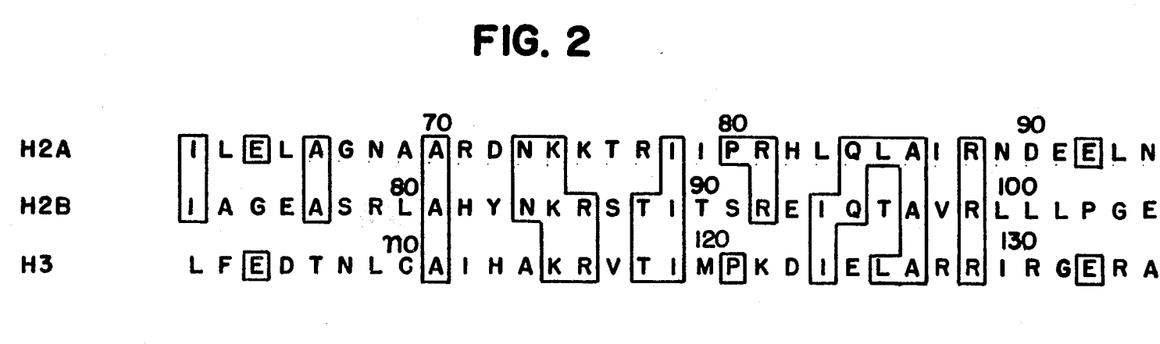
FIG. 2 shows the orientation of the C-terminal regions of the histones H2A, H2B and H3. The histones H2A and H2B were obtained from calves or humans. (Calf and human H2 histones are identical.) The H3 histone was obtained from calves. The H2A sequences 62–94, the H2B sequences 73–105 and the H3 sequences 103–135 (the C-terminal end) are compared with each other. Identical amino acids are enclosed between lines.

Attempts at a direct comparison in the N-terminal regions of the histone/HTH structures yield fewer identifies in the paired comparisons (5 or fewer per 15 amino acids). However, the homology can be increased between the different pairs being compared by introducing sequence interruptions (gaps). The N-terminal reference area, which contains the maximum number of identical groups and the minimum number of gaps, shows three other independent agreements. This area is shown in FIG. 3 (A). Another agreement lies in the fact that this part, containing only few sequence shifts, shows similarities with the C-terminal regions of the histones proper, which regions are similar to each other (FIG. 2). Furthermore, this region (FIG. 3 (A)) also covers the regions which participate in the bond interaction [29] (FIG. 3 (B)). Consequently, functional similarities proposed independent of each other can now be correlated with evident existing maximum structural identities. Finally, at the end of the regions shown in FIG. 3 (A)), HTH$_\alpha$ and HTH$_\beta$ and H2B contain Lys-Arg pairs and other dibasic structures which are considered to be typical signals of proteases which release the active hormones from their pro forms. Such signal sites in histones are of essential significance for the localization of the important active sequences with immunostimulating and/or endocrinological properties according to the present invention.

Conclusions from the purification and characterization of HTH

HTH preparations contain two components which were consistantly observed on SDS polyacrylamide gel electrophoresis. These two components are present in high yield and are in agreement with the hormonal activites of the preparations. It was also possible to determine other components, but their yields were low and variable, and these components were different from one preparation to the next. The two principal components, HTH$_\alpha$ and HTH$_\beta$, were subjected to further purification by HPLC chromatography. If HTH is not a trace component, all of the biological properties of HTH which have been described so far should be attributed to one of the two components, but also to both of them if they have synergistic or additive effects.

The structure analyses revealed that HTH$_\alpha$ and HTH$_\beta$ contain 129 and 125 amino acids, respectively, which shows a good agreement with the molecular weight estimated on the basis of SDS polyacrylamide gel electrophoresis, which is ca. 15,000. These analyses also show that the primary structures of HTH$_\alpha$ and HTH$_\beta$ are identical with the calf and human histones H2A and H2B [23]. This also explains the molecular weight of ca. 30,000 determined for HTH by exclusion chromatography, since the internal histones occur in the form of the dimeric H2A:H2B. It was not possible to find any evidence of amino-acid exchange or other modifications of the histone structures in HTH [23].

Possible hormonal properties and recently discovered functions of the histones

The discovery that HTH preparations contain the histone polypeptide chains H2A and H2B in apparently dimeric configuration as the principal components suggests that the histones may have novel hitherto unknown functions. The histone structures were therefore investigated with respect to structural similarities with other thymic hormones, histones and functionally related molecules. Since peptide hormones often originate from larger pro forms, particular attention was especially paid to possible signal sites for protein cleavages and also to interactions with histone modifications and other properties. Even though the individual observations alone are not significant, they will be discussed below in order to obtain a synopsis of the novel functional possibilities.

Structural comparisons

The similarities shown in FIGS. 2 and 3 (A) indicate a high degree of agreement between the histones and the proteins compared with them. The comparison of the individual pairs is hardly significant in itself (possibly with the exception of FIG. 2), but the combined similarities are in agreement with other observations. Related bond interactions [29] and other functional properties may suffice to explain the similarities. Compared with the identity of HTH with the histones H2 and previous comparisons [29], the structural agreements in FIG. 3 (A) show that the two histones proper represent a form of prohormones. The structures in FIG. 3 (A) are also in agreement with the existence of pro forms of the thymosins and thymopoietins, which is corroborated by the existence of a precursor stage of thymosin $\alpha_1$ [20].

Prohormone analogies

Two areas in H2B are similar to such structures which are typical for cleavage sites of prohormones, e.g., a dibasic amino-acid sequence usually of the composition Lys-Arg [21]. Such a region is Lys-Arg-Lys-Arg beginning at position 28, and another is Lys-Arg beginning at position 85. Both of them lack a subsequent pro-antisignal [22]. Both positions were predicted in the region of $\beta$ turns of the secondary structure outside an $\alpha$ helix [30], and therefore they are not apparently stabilized against proteolytic cleavage ([b 31, 32]. Dibasic structures at similar positions are also present in H2A. The first area in H2A and H2B is approximately at the end of the structural agreement between histones and thymic hormones (FIG. 3 (A)). The second area is in the C-terminal part which is identical with the region of the prealbumin according to FIG. 3 (A); it had previously been suggested that this region corresponds to the cleavage sites of gastrointestinal hormones [18].

The histones H2A and H2B were found to only permit a limited number of cleavages in vitro without preliminary denaturing. H2B is mainly split according to Lys-20 and Lys-23 [33] and H2A mainly according to Arg-11 and Lys-118 [34]. Consequently, the native conformations protect the histone molecules against complete proteolysis in a manner that is similar to the selective cleavages in prohormones. Endogenous proteases were shown which cause cleavage in the same N- and C-terminal regions [35, 36], and the corresponding H2B fragments released had a molecular weight of ca. 2000, which corresponds to the size originally described for HTH. It was inferred from this by the inventors that the thymic hormone-active part of HTH$_\beta$/H2B is located in the N-terminal region (FIG. 3 (A)), which is significant for the application according to the present invention. The existence of thymic hormone precursors is also supported by the Lys-Arg structure at the C end of thymopoietin. It becomes clear from the above considerations that the cleavage sites of the histones are significant for the localization of the biologically active sequences according to the present invention.

Chemical modifications

The histones are known to occur in chemical modified forms [37]. The serine-6 of the histone 2B is easily phosphorylated in vitro, and Ser-32 and Ser-36 can probably be phosphorylated in vitro by cAMP-dependent protein kinase(s) [38]. These two phosphorylation sites are located in the above-discussed N-terminal histone area which is essential according to the present invention. The inventors therefore concluded that the phosphorylation/dephosphorylation is involved not only in the regulation of the conformative properties of the histones in the chromatin, but also in signal regulation at the sites which are sensitive to cleavages.

Further conclusions from a functional viewpoint

Ca. 5-15% of H2A and a few percent of H2B are bound to ubiquitin [39, 40]. A relationship was observed between the binding of ubiquitin to proteins and the regulation of protein decomposition [15]. Aside from the hypothetical functions of ubiquitin in chromatin condensation or in gene expression in the nucleus, ubiquitin could therefore also act as a signal for the folding up and the subsequent selective cleavage of HTH or H2A, H2B. Since ubiquitin occurs in the nuclei of nearly all cell types, proteases specific for the thymic tissue and chemical modifications are probably necessary for the cleavages and the activities of HTH (H2A, H2B). An influence on protein catabolism and the ubiquitin functions should also be indicative of a direct relationship with several effects of HTH (H2A, H2B) on the regulatory system.

The inventors thus were the first to be able to show additional functions of H2A and H2B besides their properties as structural proteins of chromatin, and this on the basis of their considerably higher rates of binding and catabolism compared with H3, H4 and DNA [41] and based on a possible total reconstitution of the native core-histone composition after removal of H2A and H2B [42].

Interactions with a bond region

The homology of an area in thymopoietin with the bond regions of molecules and having a folded structure similar to that of the immunoglobulins had already been proposed [29]. This prior comparison was expanded by the inventors using the existing structures (FIGS. 3 (A) and 3 (B)). The inventors found that in the case of H2B, this area contains an internal repetition (regions 16–20 and 116–120 are identical) in the same manner as immunoglobulin structures are repeated at approximately the same distance. Such a structural similarity is also consistent with the known cross reactions of the antihistone antibodies with the Fc segments of the heavy chains of the immunoglobulins [43] or with a cell-surface protein on human leukocytes [44].

Conclusions

Based on the agreements shown by the inventors between the active properties of HTH and the histones H2A and H2B, it is now possible to explain hitherto unknown functions of the histones. The observations of similarities between thymic hormone and histone by the inventors are suggestive of novel interactions with ubiquitin, which are possibly indicative of the molecular mechanism of the HTH/histone function in the regulation of protein catabolism.

Finally, the evolution can be inferred from the observations made by the inventors. The related connection between the molecules belonging to the area in question could explain the similarities observed, and it can also be expanded to a "superfamily" as suggested previously [45]. Since there are signs of preferred bond regions and the release of biological activities of HTH/histones by ubiquitin or other ordinary proteins could be possible, the similarities can be explained by converging evolution. Whatever the origin of these relations which were discovered by the inventors, they do provide novel possibilities for the understanding of the interactions between HTH, histones and ubiquitin and to the creation of biologically active substances possessing thymic hormone-like properties according to the present invention, and for the specification of processes according to the present invention for producing such active substances and for the use of histones or their active sequences in medicinal and pharmaceutical preparations with standardized preparation effect.

Essential parts of the present application have been submitted by the inventors for publication in *Proceedings of the National Academy of Sciences, U.S.A.*

LITERATURE LIST

1. Bezssonoff, N. A. & Comsa, J. (1958) Ann. Endocr. 19, 222–227.
2. Bernardi, G. & Comsa, J. (1965) Experientia 21, 416–417.
3. Comsa, J. (1965) Am. J. Med. Sci. 250, 79–85.
4. Comsa, J. & Filipp, G. (1966) Ann. Instit. Pasteur 110, 365–372.
5. Comsa, J. (1973) in Thymic Hormones, ed. Luckey, T. D., (University Press. Baltimore), pp. 39–58.
6. Comsa, J. (1973) in Thymic Hormones, ed. Luckey, T. D., (University Press, Baltimore), pp. 59–96.
7. Comsa, J., Leonhardt, H. & Wekerle, H. (1982) Rev. Physiol. Biochem. Pharmacol. 92, 115–191.
8. Comsa, J., Baumann, B., Zeppezauer, M., Leonhardt, H. & Weber, N. (1979) C. R. Acad. Sc. Paris 288, 185–187.
9. Low, T. L. K. & Goldstein, A. L. (1979) J. Biol. Chem. 254, 987–995.
10. Caldarella, J., Goodall, G. J., Felix, A. M., Heimer, E. P. Salvin, S. B. & Horecker, B. L. (1983) Proc. Natl. Acad. Sci. USA 80, 7424–7427.
11. Low, T. L. K., Hu, S.-K. & Goldstein, A. L. (1981) Proc. Natl. Acad. Sci. USA 78, 1162–1166.
12. Hannappel, E., Davoust, S. & Horecker, B. L. (1982) Proc. Natl. Acad. Sci. USA 79, 1708–1711.
13. Audhya, T., Schlesinger, D. H. & Goldstein, G. (1981) Biochemistry 20, 6195–6200.
14. Pleau, J.-M., Dardenne, M., Blouquit, Y. & Bach. J.-F. (1977) J. Biol. Chem. 252, 8045–8047.
15. Hershko, A. (1983) Cell 34, 11–12.
16. Schlesinger, D. H. Goldstein, G. & Niall, H. D. (1975) Biochemistry 14, 2214–2218.
17. Burton, P., Iden, S., Mitchell, K. & White, A. (1978) Proc. Natl. Acad. Sci. USA 75, 823–827.
18. Jörnvall, H., Carlström, A., Pettersson, T., Jacobsson, B., Persson, M. & Mutt, V. (1981) Nature 291, 261–263.
19. Robey, G., Campbell, B. J. & Luckey, T. D. (1972) Infection a. Immunity 6, 682–688.
20. Haritos, A. A., Goodall, G. J. & Horecker, B. L. (1984) Proc. Natl. Acad. Sci. USA 81, 1008–1011.
21. Pradayrol, L., Jörnvall, H., Mutt, V. & Ribet. A. (1980) FEBS Lett. 109, 55–58.
22. Jörnvall, H. & Persson, B. (1983) Biosci. Rep. 3, 225–232.
23. Reichhart, R., Jörnvall, H. & Zeppezauer, M. (1984) FEBS Lett., in Druck.
24. Delange, R. J., Hooper, J. A. & Smith, E. L. (1972) Proc. Natl. Acad. Sci. USA 69, 882–884.
25. Olson, M. O. J., Jordan, J. & Busch, H. (1972) Biochem. Biophys. Res. Commun. 46, 50–55.
26. Kanda, Y., Goodmann, D. S., Canfield, R. E. & Morgan, F. J. (1974) J. Biol. Chem. 249, 6796–6805.
27. Jörnvall, H., Mutt. V. & Persson, M. (1982) Hoppe-Seyler's Z. Physiol. Chem. 363, 475–483.

28. Ball, D. J., Slaughter, C. A., Hensely, P. & Garrard, W. T. (1983) FEBS Lett. 154, 166–170.
29. Hahn, G. S. & Hamburger, R. N. (1981) J. Immunol. 126, 459–462.
30. Moss, T., Cary, D. P., Abercrombie, B. D., Crane-Robinson, C. & Bradbury, E. M. (1976) Eur. J. Biochem. 71, 337–350.
31. Geisow, M. J. & Smyth, D. G. (1980) in The Enzymology of Post-translational Modification of Proteins, Vol. 1 (Ed.: Freedman, R. B. & Hawkins, H. C.) Academic Press, London, pp. 259–287.
32. Jörnvall, H., Ekman, R., Carlquist, M. & Persson, B. (1984) in Biogenetics of Neurohormonal Peptides (Eds.: Hakanson, R. & Thorell, J.) Academic Press, London, in press.
33. Böhm, L., Briand, G., Sautière, P. & Crane-Robinson, C. (1982) Eur. J. Biochem. 123, 299–303.
34. Böhm, L., Crane-Robinson, C. & Sautière, P. (1980) Eur. J. Biochem. 106, 525–530.
35. Rill, R. L. & Oosterhof, D. K. (1982) J. Biol. Chem. 257, 14875–14880.
36. Eickbush, T. H., Watson, D. K. & Moudrianakis, E. N. (1976) Cell 9, 785–792.
37. Isenberg, I. (1979) Ann. Rev. Biochem. 48, 159–191.
38. Yeaman, S. J., Cohen, P., Watson, D. C. & Dixon, G. H. (1977) Biochem. J. 162, 411–421.
39. Busch, H., Ballal, N. R., Busch, R. K., Choi, Y. C., Davis, F., Goldknopf, I. L., Matsui, S. I. Rao, M. S. & Rothblum, L. J. (1978) Cold Spring Harbor Symp. Quant. Biol. 42, 665–683.
40. West, M. H. P. & Bonner, W. M. (1980) Nucl. Acids Res. 8, 4671–4680.
41. Grove, G. W. & Zweidler, A., (1984) Biochemistry 23, 4436–4443.
42. Jordano, J., Montero, F. & Palacian, E. (1984) Biochemistry 23, 4280.
43. Hannestad, K. & Stollar, B. D. (1978) Nature 275, 671–673.
44. Rekvig, O. P. & Hannestad, K. (1980) J. Exp. Med. 152, 1720–1733.
45. Williams, A. F. (1984) Nature 308, 12–13.

What is claimed is:

1. A therapeutic method for the stimulation of the immune system of a patient in need thereof which comprises administering to said patient a biological composition which comprises a therapeutically acceptable carrier and, in quantity having an immuno-stimulating effect, a biologically active pure histone selected from the group consisting of H2A, H2B, and an evolutionary variable amino acid sequence thereof.

2. The method of claim 1, wherein the histone administered is free of the constant non-evolutionary variable amino acid sequence.

3. The method of claim 1 or 2 wherein the histone is H2A.

4. The method of claim 1 or 2 wherein the histone is H2B.

5. The method of claim 1 or 2 wherein the histone contains an evolutionary variable sequence of H2A or H2B.

6. A therapeutic method for the treatment of the immune system of a patient in need thereof comprising administering to the patient a biological composition which comprises a therapeutically acceptable carrier and, in a quantity having an immuno-therapeutic effect, at least one biologically-active pure histone selected from the group consisting of H2A, H2B, and an evolutionary variable amino acid sequence thereof.

7. The method of claim 6 wherein the histone is H2A.

8. The method of claim 6 wherein the histone is H2B.

9. The method of claim 6 wherein the histone is an evolutionary variable amino acid sequence of H2A or H2B.

10. A composition comprising a biologically-active pure histone selected from the group consisting of H2A and H2B, and ubiquitin.

11. The composition of claim 10 wherein the histone contains the evolutionary variable sequence thereof.

12. The composition of claim 10 or 11 wherein the histone is extracted from an endocrine gland.

13. The composition of claim 12 wherein the gland is calf thymus.

14. The composition of claim 10 wherein the histone exhibits thymic-hormone-like properties.

15. A biologically-active composition comprising the evolutionary variable sequence of a pure histone selected from the group consisting of H2A and H2B, and ubiquitin.

16. The composition of claim 11 or 15 wherein the evolutionary variable sequence includes the amino acid sequence of 1 to 36 amino acids.

17. The composition of claim 11 or 15 wherein the evolutionary variable sequence is free of the constant evolutionary sequence.

18. The composition of claim 15 wherein the evolutionary variable sequence is the histone sequence of H2A.

19. The composition of claim 18 wherein the evolutionary variable sequence consists essentially of an amino acid sequence of 1 to 36 amino acids.

20. The composition of claim 15 wherein the evolutionary variable sequence is the histone sequence of H2B.

21. The composition of claim 15 wherein the histone exhibits thymic-hormone-like properties.

22. The composition of claim 15 wherein the histone is extracted from an endocrine gland.

23. The composition of claim 22 wherein the gland is calf thymus.

* * * * *